United States Patent [19]

Voelz

[11] Patent Number: 4,940,059
[45] Date of Patent: Jul. 10, 1990

[54] POLYGRAPH WITH IMPROVED CARDIAC MONITORING

[75] Inventor: Michael H. Voelz, Battle Ground, Ind.

[73] Assignee: Lafayette Instrument Co., Inc., Lafayette, Ind.

[21] Appl. No.: 170,743

[22] Filed: Mar. 21, 1988

[51] Int. Cl.$^5$ .............................................. A61N 1/00
[52] U.S. Cl. .................................. 128/688; 128/900; 128/695
[58] Field of Search ............... 128/695, 687, 688, 731, 128/734, 900, 682, 683

[56] References Cited

U.S. PATENT DOCUMENTS

| 2,658,505 | 11/1953 | Sheer .................................. 128/687 |
| 2,944,542 | 7/1960 | Barnett et al. ....................... 128/688 |
| 4,418,700 | 12/1983 | Warner ................................ 128/672 |
| 4,564,020 | 1/1986 | Link ................................... 128/688 |
| 4,821,735 | 4/1989 | Goor et al. .......................... 128/672 |

OTHER PUBLICATIONS

Measurement of the Maximum Rate of Rise of Aortic Blood Pressure in Man, by George et al., Medical Research Engineering, Fourth Quarter, 1967.

Primary Examiner—Francis Jaworski
Assistant Examiner—George Manuel
Attorney, Agent, or Firm—Andrus, Sceales, Starke & Sawall

[57] ABSTRACT

A polygraph for detecting and displaying the beat by beat changes in the relative rate of increase of the blood pressure of the heart. Electronic circuitry for measuring the derivative of the blood pressure pulse, and displaying it on either a separate channel or by adding it to the top of the blood pressure pulse waveform from which it was derived is disclosed.

10 Claims, 12 Drawing Sheets

POLYGRAPH WITH IMPROVED CARDIAC MONITORING

BACKGROUND OF THE INVENTION

The present invention relates to polygraphs, and more particularly to a polygraph with an improved cardiac monitoring channel.

Instruments for detecting and measuring physiological changes that accompany emotional stress are well known under the commonly used term of lie detectors. Such instruments are also often called polygraphs, and generally consist of sensors physically connected to an individuals body for measuring various physiological parameters. Standard sensors include a blood pressure cuff, a pair of respiration belts, and skin resistance finger electrodes, all suitably coupled to recording pins traversing a record chart. Examples of such instruments and polygraph measuring systems can be found in the following U.S. Pats:

| U.S. Pat. No. | Inventor | Issue Date |
| --- | --- | --- |
| 1,472,016 | Dressler | 10-23-23 |
| 2,235,894 | Lee | 03-25-41 |
| 2,655,425 | Wood | 10-13-53 |
| 2,944,542 | Barnette et al | 07-12-60 |
| 3,850,169 | Gebben et al | 11-26-74 |
| 3,908,641 | Judson et al | 09-30-75 |
| 3,915,156 | Wastl et al | 10-28-75 |
| 4,085,740 | Allen, Jr. | 04-25-78 |
| 4,178,918 | Cornwell | 12-18-79 |
| 4,219,028 | Lencioni, Jr. | 08-26-80 |
| 4,442,845 | Stephens | 04-17-84 |
| 4,520,232 | Wilson | 05-28-85 |

When utilizing a polygraph for detecting deception, an examiner must be skilled in the ability to formulate appropriate questions which will cause a subject to physiologically react to those questions in order to indicate that the subject is not being truthful. In addition to the skill of the examiner, the polygraph or lie detector instrument must be able to detect these subtle changes in the state of the subject which accompany the physiological changes associated with the subject being untruthful. The above noted standard channels monitored by the lie detector instrument are traditionally considered to be under the control of the subject's autonomic nervous system and therefore not under the physical or conscious control of the subject. The basic idea is that when a subject becomes aroused by being asked questions the subject does not truthfully answer or questions which cause the subject to become aroused in general, the lie detection instrument will display changes in the noncontrollable physiologic parameters of the subject. The examiner can use these displayed changes to determine if the subject is aroused by the subject matter of the questions as an aid in detecting deception.

In a polygraph, the mechanical cardio channel has an ink pen over-shoot. The over-shoot of the ink pen of the mechanical cardio channel comes at the top of the blood pressure pulse, and is the result of the momentum of the mass of the ink pen which is produced during the reproduction of the rapid upstroke of the blood pressure pulse during a heart contraction. The ink pen, in the mechanical cardio channel, is directly connected to a blood pressure cuff which is wrapped around the upper arm of the subject. This blood pressure cuff is air inflated to couple the cuff to the brachial artery. When the heart contracts, it rapidly generates pressure which pumps or circulates blood to the body. This blood pressure pulse wave travels down the aorta, which is the main body artery, and is what is sensed by the blood pressure cuff around the subject's arm. The blood pressure wave has a characteristic periodic waveform which can be discussed in standard physiologic terminology. The waveform begins with an atrial contraction which is not always visible and which is usually seen in young people who have very elastic arteries and heart valves. Following the contraction of the atrium, the ventricles contract, pumping blood out of the heart to the lungs and general body circulation. The maximum pressure produced by the left ventricle is termed the systolic blood pressure and is represented by the peak of the blood pressure pulse waveform. Since the aorta is elastic, it is stretched by the blood being pumped from the left ventricle during contraction. Thereafter, the heart relaxes and blood pressure begins to fall. As the heart relaxes, blood is pushed back into the heart and out to the body by the stretched aorta. The entrance to the aorta has a one-way valve called the aortic valve which closes and stops blood from flowing back into the heart. The closing of this valve is what causes the dicrotic notch in the blood pressure pulse waveform. The diastolic run-off indicates the rate of blood flow out of the stretched aorta to the body. Finally, just before the beginning of the next heart beat, the blood pressure in the arteries drops to its lowest level which results in what is termed the diastolic blood pressure.

The ink pen over-shoot of the mechanical cardio channel, referred to above, is the result of the rapid pressure rise when the heart contracts. The rate of this pressure rise is an indication of the strength of contraction of the left ventricle. The strength of contraction of the left ventricle of the heart is determined by many things, such as (1) the strength of the heart muscle; (2) the heart rate; (3) the amount of blood that is in the left ventricle; (4) the resistance to the flow of blood in the body (the peripheral resistance); (5) the elasticity of the aorta; and (6) the state of excitation of the subject. These parameters are not under the conscious control of the subject, and for this reason, it would be desirable to obtain a measurement of the rate of blood pressure increase in order to provide an additional aid to an examiner for indicating deception by a polygraph subject.

SUMMARY OF THE INVENTION

A polygraph for detecting and recording physiological changes in an individual includes sensing means for sensing a physiological condition of an individual, control means operably connected to the sensing means for determining the rate of change over time of the physiological condition, and display means operably connected to the control means for displaying a signal indicative of the rate of change over time of the physiological condition. The apparatus may be utilized to monitor the rate of change over time of various physiological conditions such as respiration, skin resistance, or blood pressure, and is particularly suitable for use in connection with measuring changes in the rate of blood pressure increase during a ventricular contraction.

The polygraph of the present invention detects and displays the beat by beat changes in the relative rate of increase of the blood pressure of the left side of the heart. This may be called a measure of the contractility of the heart or the strength of contraction of the heart and may be measured by taking the derivative of the blood pressure pulse waveform. The derivative is the rate, per unit time, of the increase of pressure of the arterial blood and is represented by the symbol dP/dt of the blood pressure.

The improved cardiac monitoring provided by the present invention displays an indication of the rate of blood pressure increase i.e. dP/dt, on a beat by beat basis and therefore shows an examiner how the strength of contraction of the heart is varying, relative to itself, after each heart beat. The intended purpose of this information is to allow the examiner to be able to determine whether the subject is being truthful or is aroused by the questions, with even better accuracy than may be accomplished with the existing polygraph channels. By giving a polygraph examiner this additional channel of information, that is different than any existing available information, the accuracy with which the examiner can determine if a subject is being truthful may be increased. Thus, by monitoring changes in dP/dt of the blood pressure during questioning in a polygraph examination, it may be possible to determine when a subject is answering truthfully and when the subject is being deceptive. When a subject is answering truthfully, changes in dP/dt should show a smooth pattern associated with the subjects respiration. When the subject is being deceptive, the dP/dt signal should show greater change because of (1) changes in the breathing pattern; (2) release of catecholamines which are part of the "fight or flight" response and which stimulate the heart; (3) change in peripheral resistance, which is also due to the release of catecholamines which alter the hydraulic resistance that the heart is pumping against; and (4) changes in the amount of blood being supplied to the left ventricle. This blood stretches the left ventricle and determines how vigorous the contraction is (Starling's Law).

In one aspect of the invention, the control circuitry for indicating changes in dP/dt includes means for detecting the dP/dt signal and then displaying the dP/dt signal on a separate polygraph channel. This display would show relative changes in the level of dP/dt from one cardiac contraction to the next. Basically, this control circuitry includes differentiator means for producing a differential signal indicative of a change in dP/dt, measuring means for measuring a desired parameter of the differential signal over a given time interval and for providing a pen driving signal, and timing means for determining the appropriate time interval. Preferably, the measuring means measures the amplitude of the dP/dt signal and includes a detector means for detecting the peak differential signal and a sample and hold circuit means operable between a sample mode for receiving the peak differential signal and a hold mode for holding the peak differential signal which provides the pen driving signal.

In another aspect of the invention, the control circuitry indicates the relative level of the dP/dt from one heart beat to the next and adds the indication of this level to the top of the blood pressure waveform polygraph channel. Thus, this latter aspect of the invention simulates electronically upon the blood pressure waveform the ink pen over-shoot of the polygraph mechanical cardio channel. In order to accomplish this, the control circuitry includes a delay circuit for receiving the blood pressure pulse signal and producing a delayed blood pressure pulse signal, summing means for summing the delayed blood pressure pulse signal and the peak differential signal, switch means operable between a closed position to turn on the summing means to permit summing of the delayed blood pressure pulse signal and the peak differential signal and an open position to turn off the summing means, and a trigger circuit for triggering the switch means at any desired time during the blood pressure pulse signal. In this manner, the relative dP/dt value may be added to the blood pressure pulse waveform at any location on the blood pressure pulse waveform.

Other features and advantages of the invention will become apparent to those skilled in the art upon reviewing the following detailed description, the drawings, and the impended claims.

BRIEF DESCRIPTION OF THE DRAWINGS

The drawings illustrate the best mode presently contemplated of carrying out the invention.

In the drawings.

DESCRIPTION OF THE PREFERRED EMBODIMENTS

Figure 1:
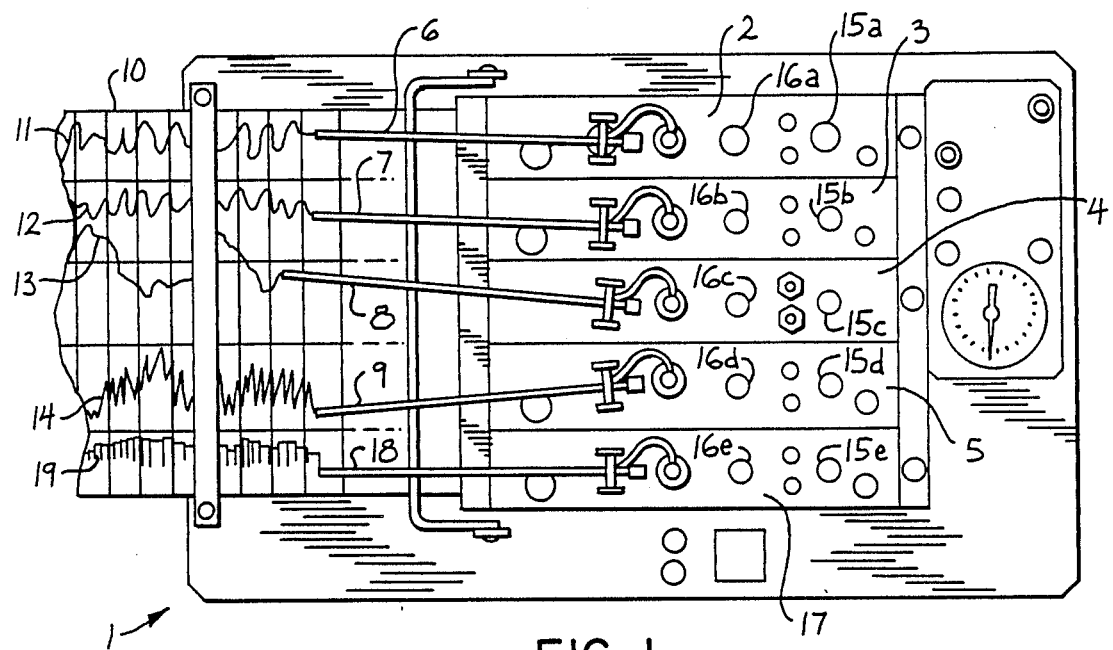
FIG. 1 is a plan view of a polygraph incorporating a first embodiment of the cardiac monitoring apparatus of the present invention.

Referring now to the drawings, FIG. 1 illustrates a polygraph generally designated by the numeral 1. Polygraph 1 includes a plurality of electronic modules 2-5 suitably coupled to recording pens 6-9, respectively, which traverse a record chart or strip chart 10. Modules 2-5 are typically employed to detect and measure physiological changes in an individual that accompany emotional stress during a lie detection examination. For example, module 2 may be employed to monitor chest respiration changes in a manner as is shown by waveform 11 on chart 10. Module 3 on the other hand may be employed to detect and record abdominal respiration changes as shown by waveform 12. Module 4 may be employed to measure skin resistance in a manner as shown by waveform 13. Finally, module 5 may be employed to monitor blood pressure changes of the subject being examined as shown by waveform 14.

In order to provide a more accurate indication of the physiological changes occurring in response to emotional stress, an examiner must be able to adjust the sensitivity or amplitude of waveforms 11-14 as well as control the balance or centering on chart 10 of waveforms 11-14. In order to accomplish this, modules 2-5 each include a sensitivity control 15a-15d as well as a balance or centering control 16a-16d, respectively. Sensitivity controls 15a-15d balance controls 16a-16d each consist of a variable potentiometer comprising an adjustable wiper which moves between extremes of a potentiometer range. Thus, rotation of the appropriate control knob by an examiner will move the wiper of the control potentiometer to change or adjust waveforms 11-14, as desired.

As shown in FIG. 1, polygraph 1 also includes a fifth module 17 suitably coupled to a recording pen 18 which also traverses chart 10 to produce a waveform 19 which is indicative of the changes in the relative rate of increase of the blood pressure of the left side of the heart. This might be called a measure of the contractility of the heart and is represented as dP/dt of the blood pressure. Waveform 19 displays a positive square wave and provides an indication of the changes in the relative rate of increase of the blood pressure of the left side of the heart on a beat by beat basis and therefore shows an examiner how the strength of contraction of the heart is varying, relative to itself, after each heart beat. The size, location, and shape of the pulse amplitude and pulse width of waveform 19 may be adjusted as desired by the examiner with a sensitivity control 15e and a balance control 16e.

Figure 2:
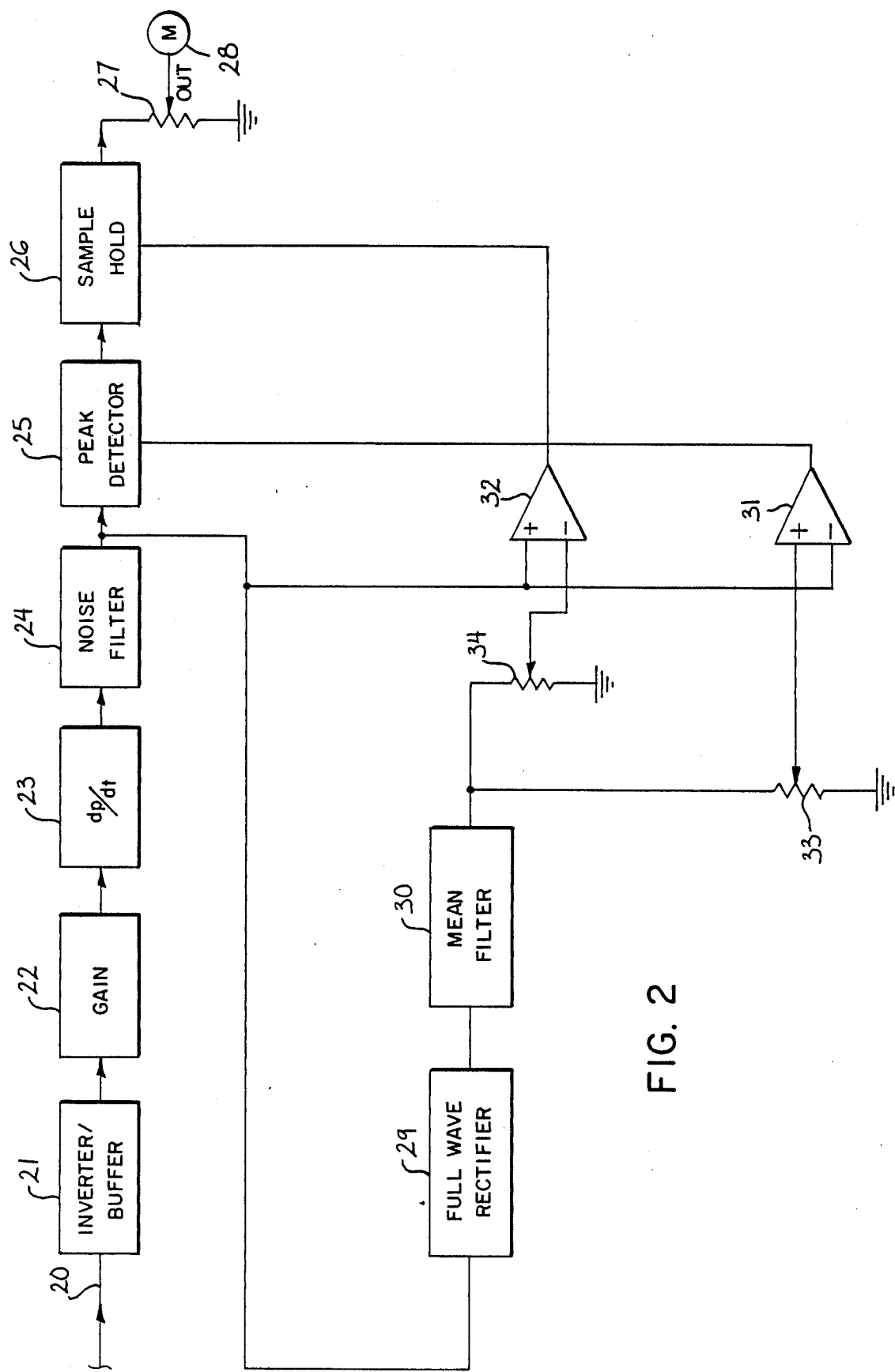
FIG. 2 is block diagram of the electronic circuitry for the cardiac monitoring apparatus of FIG. 1.

FIG. 2 illustrates a block diagram for the electronic circuitry for detecting and displaying the changes in dP/dt for each heart beat. The source signal, designated by the numeral 20, is obtained from the traditional polygraph cardio channel and is the relative blood pressure pulse of the subject being examined. This relative blood pressure pulse signal 20 is detected from a blood pressure cuff (not shown) which is typically wrapped around the arm of the subject being examined. Signal 20 is isolated or separated from the normal amplifier circuit of polygraph module 5 by means of a buffer circuit 21 and inverted if necessary. The signal from buffer circuit 21 is then amplified via gain circuit 22 and fed into a differentiator circuit 23 which electronically produces a derivative of the signal. The signal, which is now a derivative, passes through a low pass filter 24 to remove noise from the differential signal, and is then fed to a peak detector circuit 25 which detects the peak of the derivative signal and sends that peak voltage level to a sample and hold circuit 26 which holds the peak level of the derivative signal. This peak voltage level signal is then fed into a potentiometer 27 allowing the amplitude of the signal to be adjusted before it is fed to a motor 28 for driving pen 18.

The timing for peak detector circuit 25 and sample and hold circuit 26 is achieved by using a rectifier circuit 29 which receives the differentiated and filtered signal and causes all the pulses of the derivative signal to be positive. The signal from rectifier circuit 29 is then passed through mean filter circuit 30 to derive an average level of the voltage level of the rectified derivative signal. The average level is then sent to a comparator circuit which includes a pair of comparators 31, 32 which compare the voltage level of the average signal to the voltage level of the actual derivative signal. Comparator 31 is utilized for the peak detector circuit 25 and comparator 32 is utilized for the sample and hold circuit 26. The timing is set so that the peak detector circuit 25 is holding the voltage level of the last derivative peak when the sample and hold circuit 26 is in its sample mode. Thus, the level of the peak voltage of the last heart beat upstroke rate is held on the record until the next heart beat comes along. The level of the mean dP/dt signal being fed to comparators 31, 32 is adjustable by means of a pair of potentiometers 33, 34 respectively so that this mean dP/dt signal can be set to any level down to zero volts, or up to a level greater than the level of the dP/dt signal (because the mean producing filter circuit 30 has gain).

Waveform 19 on chart 10 thus consists of a series of steps or square wave pulses which show the relative level of the dP/dt signal for each heart beat comparable to the other heart beat levels. In the detection of deception, it is desirable to show changes in the physiological parameters being monitored as the subject is asked questions. As a result, waveform 19 does not have to show absolute values of the dP/dt, but rather, it has to indicate to the examiner when the monitored variable changes in conjunction with the questions being asked.

Figure 3A:
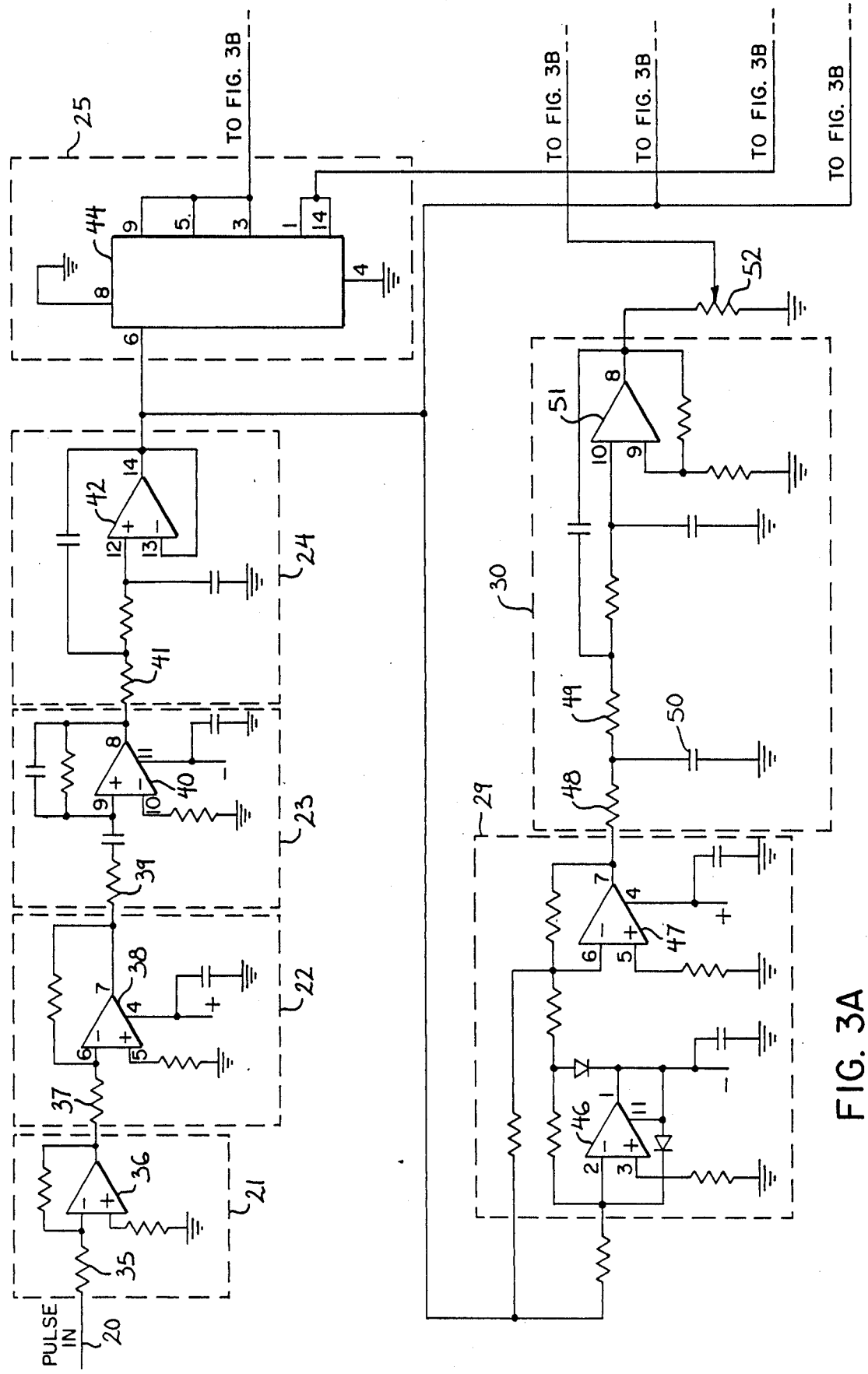
FIGS. 3A-3B are schematic diagrams of the electronic circuitry for the cardiac monitoring channel of the polygraph of FIG. 1.
Figure 3B:
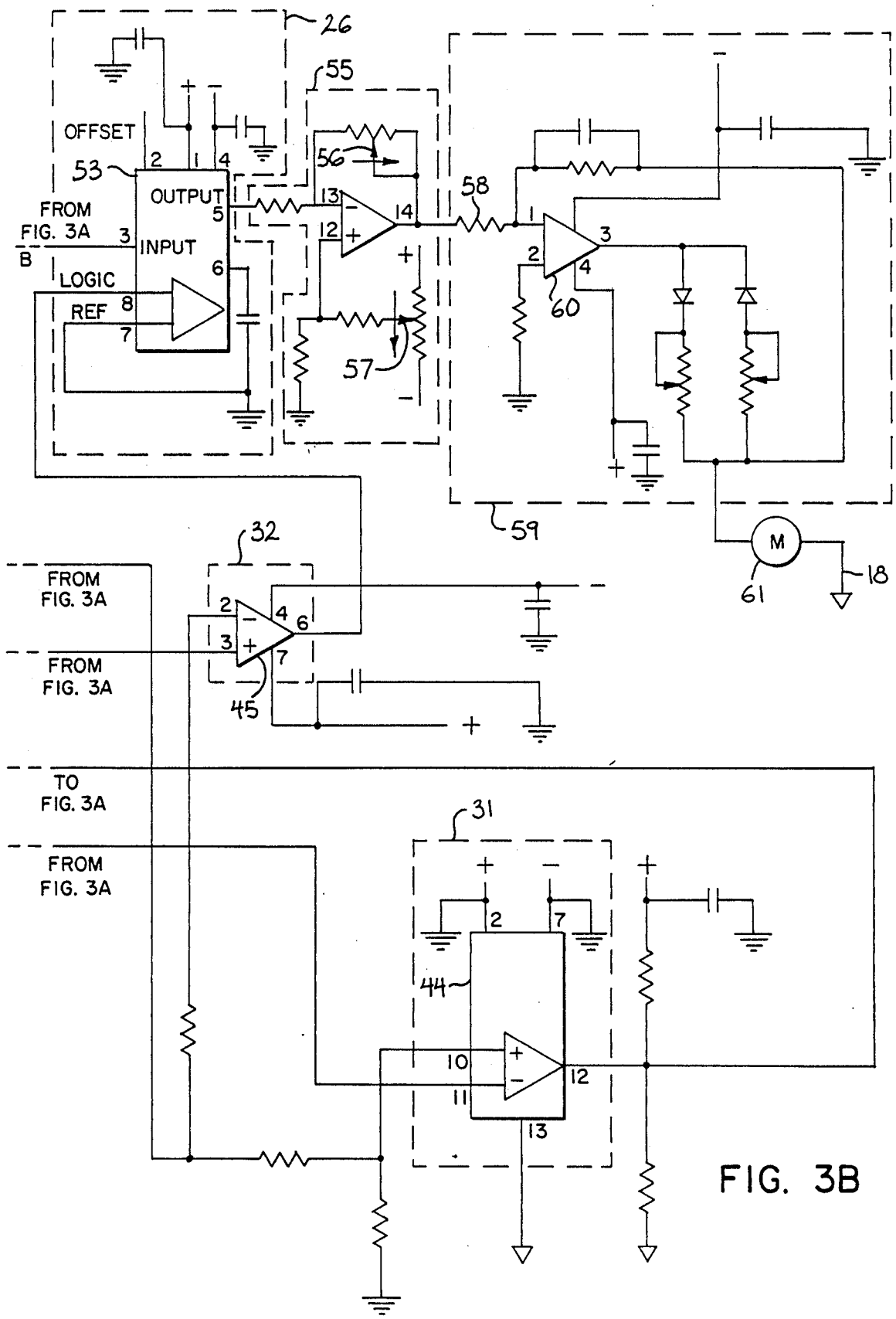

Referring now to FIGS. 3A and 3B, there is shown in detail the control circuitry for detecting, measuring and displaying changes in the rate of blood pressure increase of a subject being examined by means of polygraph 1. Blood pressure pulse signal 20 is first passed to a buffer amplifier 36 which isolates and inverts the signal before going to the circuitry shown in FIGS. 3A and 3B from the normal amplifier circuit of polygraph module 5. Amplifier 36 may, for example, be a Motorola LM 324 or a Linear Technology 1014. Buffer amplifier 36 may also be a noninverting buffer for signal 20 if necessary. The signal from buffer amplifier 36 then passes into gain circuit 22. Gain circuit 22 includes an operational amplifier 38 which amplifies the signal before it is sent to differentiator circuit 23. Amplifier 38 may comprise a Linear Technology 1014 or a Motorola LM 324 or any similar operational amplifier integrated circuit. The signal from amplifier 38 then passes to differentiator circuit 23. Differentiator circuit 23 includes an operational amplifier 40 which may be a Linear Technology 1014 or a Precision Monolithics OPA27 or any other suitable integrated circuit operational amplifier. Differentiator circuit 23 detects the changing voltage level of the blood pressure pulse signal 20 and is configured with gain to provide derivative voltage out of signal 20 voltages. The differential output voltage is then passed to a low pass filter 24 to remove noise from the differential signal. Filter 24 includes an operational amplifier 42 which may be a Linear Technology 1014 or any similar operational amplifier. The output from low pass filter 24, which is the filtered differential signal, is then transmitted to four different places. First, the signal is sent to peak detector circuit 25 which may comprise a monolithic integrated circuit such as model PKD01 available from Precision Monolithics or a standard peak detector circuit which is readily commercially available. Secondly, the differential signal is sent to one side of comparator 31 (See FIG. 3B) which in this embodiment comprises part of model PKD01 integrated circuit 44 available from the Precision Monolithics Company. Thirdly, the differential signal is sent to comparator 32 (See FIG. 3B) which as shown is an operational amplifier 45 model 741 available from the Motorola Company but which can be any similar operational amplifier. Lastly, the differential signal is sent to rectifier circuit 29. Rectifier circuit 29 includes a pair of Linear Technology Model 1014 operational amplifiers 46, 47 or any similar operational amplifiers. Rectifier circuit 29 takes the differential output signal, which may be swinging plus and minus relative to zero, and converts the signal to always be positive. After being rectified, the signal from circuit 29 is fed to mean filter circuit 30. Filter circuit 30 comprises a third order low pass filter, with gain, and includes amplifier 51 which may be a Linear Technology Model 1014 or any similar device. Filter circuit 30 has a cut-off frequency low enough to produce a mean value, or average value, of the differential signal which is periodic in nature. The output from mean filter circuit 30 is then fed to a potentiometer 52 which is used to calibrate the trip point for comparators 31, 32. Thus, the output from filter circuit 30 may be termed the "mean dP/dt signal", and this mean dP/dt signal may be adjustable by potentiometer 52 so that it can be set to any level down to zero volts, or up to a level greater than the level of the dP/dt pulse from filter circuit 24 (because the mean producing filter circuit 30 has gain).

Referring now more specifically to FIG. 3B, it can be seen that one side of comparator 31 receives the differential signal from filter circuit 24, and the other side of comparator 31 receives the mean dP/dt signal from mean filter circuit 30. Likewise, one side of comparator 32 receives the differential signal from filter circuit 24 and the other side thereof receives the mean dP/dt signal from mean filter circuit 30. As is conventional, comparators 31, 32 will give a signal out whenever the signal in on one side thereof changes relative to the signal on the other side thereof. As shown best in FIG. 3B, the output of comparator 32 is fed to sample and hold circuit 26 while the output of comparator 31 is fed to peak detector circuit 25. For the peak detector circuit 25, the mean dP/dt voltage signal is fed into the positive side of the comparator and the actual differential pulse or dP/dt signal is fed into the negative side of comparator 31. When the voltage of the actual dP/dt pulse is above the voltage of the mean dP/dt signal, the output of comparator 31 goes low which triggers integrated circuit 44 to hold the peak value of the actual dP/dt pulse. When the voltage level of the actual dP/dt pulse drops below the voltage of the mean dP/dt signal, the output of comparator 31 goes high which resets the integrated circuit 44.

For sample and hold circuit 26, comparator 32 is set up just the opposite from comparator 31. In this case, when the actual dP/dt voltage signal exceeds the voltage signal of the mean dP/dt pulse, the output of comparator 32 goes high so that sample and hold circuit 26 is in a sample mode. When the actual dP/dt voltage signal drops below the mean dP/dt voltage level, the output of comparator 32 goes low so that sample and hold circuit 26 is in its hold mode. The trip levels of comparators 31, 32 are set so that sample and hold circuit 26 has gone into its hold mode before peak detector circuit 25 is reset. This allows sample and hold circuit 26 to hold the peak level of the actual dP/dt signal until the next heart beat at which point the entire process starts over. The value being held by the sample and hold circuit 26 is what is displayed as waveform 19 by module 17 of polygraph 1.

As shown best in FIG. 3B, sample and hold circuit 26 comprises a monolithic integrated circuit 53 which may be a Model LF398 available from the National Semiconductor Company or may be any similar integrated circuit or may be made of discrete components, if desired. The output from integrated circuit 53 passes to a signal size adjustment circuit 55 which allows a user to adjust not only the size or amplitude of waveform 19 by means of a knob connected to wiper 56, but also to center waveform 19 on chart 10 by means of wiper 57 so that the user may move pen 18 anywhere on chart 10. The output from circuit 55 connects to a pen motor drive circuit 59, which as shown, includes an operational amplifier 60 which may be a Model 759 available from the Fairchild Company or any similar circuit. Pen motor drive circuit 59 provides sufficient current to drive pen motor 61 which in turn drives pen 18 to produce waveform 19.

Figure 4:
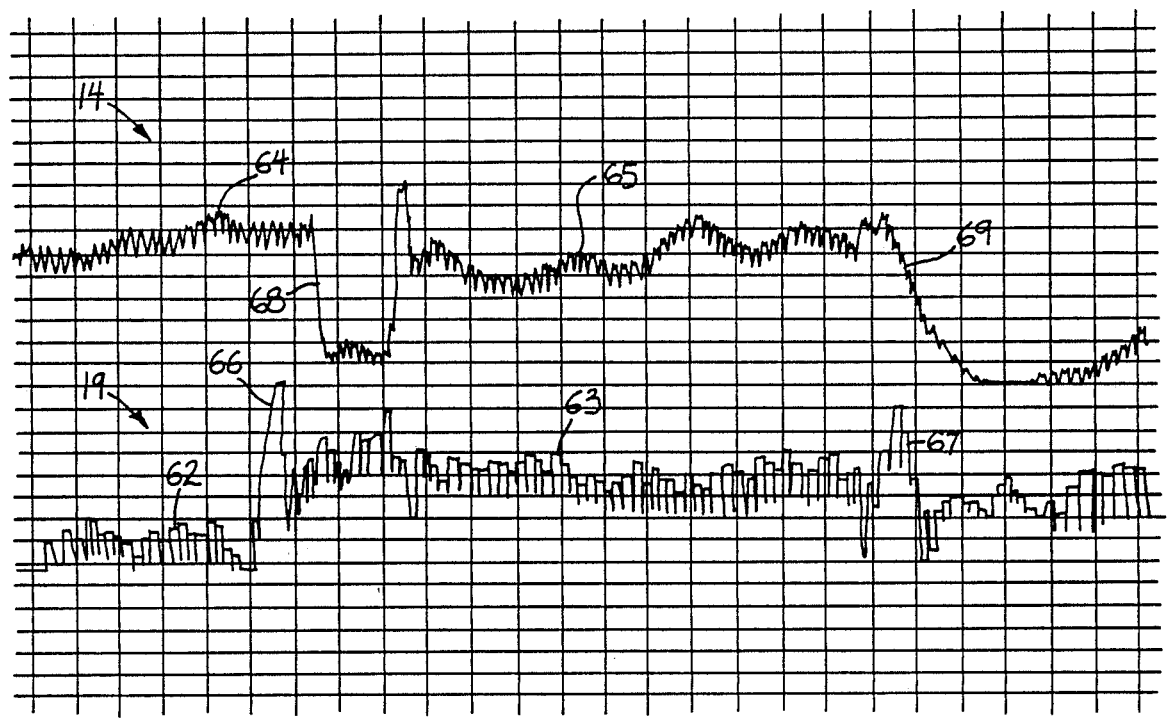
FIG. 4 is a diagram illustrating a record produced by the cardiac monitoring circuitry of FIGS. 3A-3B.

Referring now to FIG. 4, there is illustrated a sample record obtained by utilizing the circuitry shown in FIGS. 3A-3B to produce waveform 19 as well as the conventional circuitry to produce blood pressure waveform 14. Note that in the areas generally designated by the numerals 62 and 63, the changes in dP/dt show a smooth pattern associated with the subjects respiration and heart beat which corresponds to the smooth pattern illustrated in portions 64, 65 respectively of waveform 14. However, in the areas of waveform 19 generally designated by the numerals 66 and 67, the dP/dt signal shows a greater change, and corresponds to the changes in blood pressure pulse waveform 14 noted generally at 68, 69 respectively. Area 66 of waveform 19 and area 68 of waveform 14 were caused as the result of a Valsalva meneuver on the part of the subject being examined to produce the record of FIG. 4. A valsalva meneuver is one in which the subject forcibly tries to exhale against a closed glottis. In turn, the area 67 of waveform 19 at 69 of waveform 14 were the result of the subject taking a deep breath during the examination.

Figure 5:
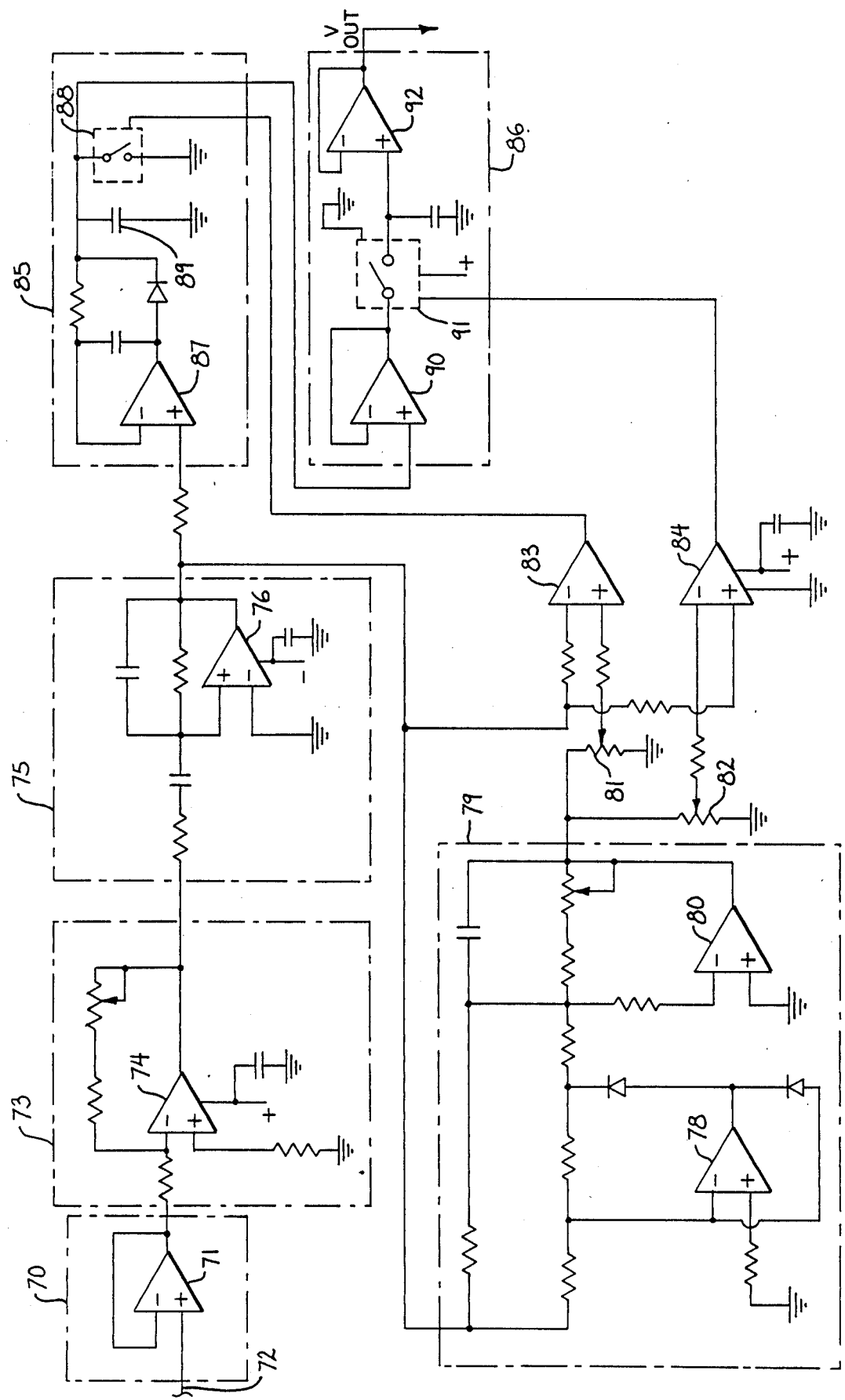
FIG. 5 is a schematic diagram of a second embodiment of the electronic circuitry for the cardiac monitoring apparatus of FIG. 1.

Referring now to FIG. 5, there is illustrated a schematic diagram of an alternate electronic circuit corresponding to the block diagram of FIG. 2 for producing waveform 19. The basic difference between the circuitry of FIG. 5 and the circuitry of FIGS. 3A-3B is that the integrated circuits 44 and 53 are replaced by discreet component circuitry. Thus, the circuitry shown in FIG. 5 includes a buffer circuit 70 which may include a Motorola LM324 amplifier or similar component 71 to take blood pressure pulse signal 72 from a standard cardio polygraph channel and isolate and/or invert (if required using a slightly different circuit layout) signal 72. The output from buffer circuit 70 passes through a gain circuit 73 which includes a Motorola LM324 amplifier or similar component 74 which functions to amplify the output from buffer circuit 70 to drive an electronic differentiator circuit 75. Differentiator circuit 75 includes a Precision Monolithics OPA27 amplifier or similar component 76 which detects the changing voltage level of blood pressure pulse signal 72 from circuit 73 and is configured with gain to provide a derivative voltage out of the changing voltage detected. The differential output signal is then sent to a rectifier/filter circuit 79 having a Motorola LM324 amplifier or similar component 78 and 80 in order to produce a mean value of the derivative signal. The mean value of the derivative signal is then passed through a pair of potentiometers 81, 82 and comparators 83, 84, respectively, which control a peak detector circuit 85 and sample and hold circuit 86 in the same manner as previously described with respect to the circuitry of FIGS. 3A-3B.

In the embodiment of FIG. 5, peak detector circuit 85 includes a Texas Instrument TL082 amplifier or similar component 87 together with a Motorola 4066 switch or similar component 88 and a hold capacitor 89. With respect to sample hold circuit 86 this circuit includes a Texas Instrument TLC251 amplifier or similar component 90 whose output is connected to a Motorola 4066 switch or similar component 91 which is in series with a second Texas Instrument 251 amplifier or similar component 92. The output from amplifier 92 is utilized to drive pen 18 of module 17 of polygraph 1 to produce waveform 19.

In operation, the mean dP/dt signal from mean filter circuit 79 is fed into the positive side of comparator 83 and the actual dP/dt signal from differentiator circuit 75 is fed into the negative side of comparator 83. When the voltage of the differentiated signal is above the voltage of the mean dP/dt signal, comparator 83 output goes low which opens switch 88 of peak detector circuit 85 allowing circuit 85 to hold the peak value of the actual dP/dt pulse. When the voltage level of the actual dP/dt signal from differentiator circuit 75 drops below the voltage of the mean level signal from circuit 79, comparator 83 goes high which resets peak detector circuit 85. With respect to the sample and hold circuit 86, comparator 84 is set up just the opposite from comparator 83. In other words, the actual dP/dt signal from differentiator circuit 75 is fed into the positive side of comparator 84 and the mean level dP/dt signal from circuit 79 is fed into the negative side of comparator 84. Thus, when the actual dP/dt voltage exceeds the voltage of the mean dP/dt signal, comparator 84 output goes high to close switch 91 and place sample and hold circuit 86 in its sample mode. When the actual dP/dt voltage level drops below the mean voltage level, the output of comparator 84 goes low which opens switch 91 so that circuit 86 is in its hold mode. The trip levels are set so that the sample and hold circuit 86 goes into its hold mode before the peak detector circuit 85 is reset. This allows the sample and hold circuit 86 to hold the peak level of the dP/dt signal until the next heart beat at which point the whole process starts over.

Figure 6:
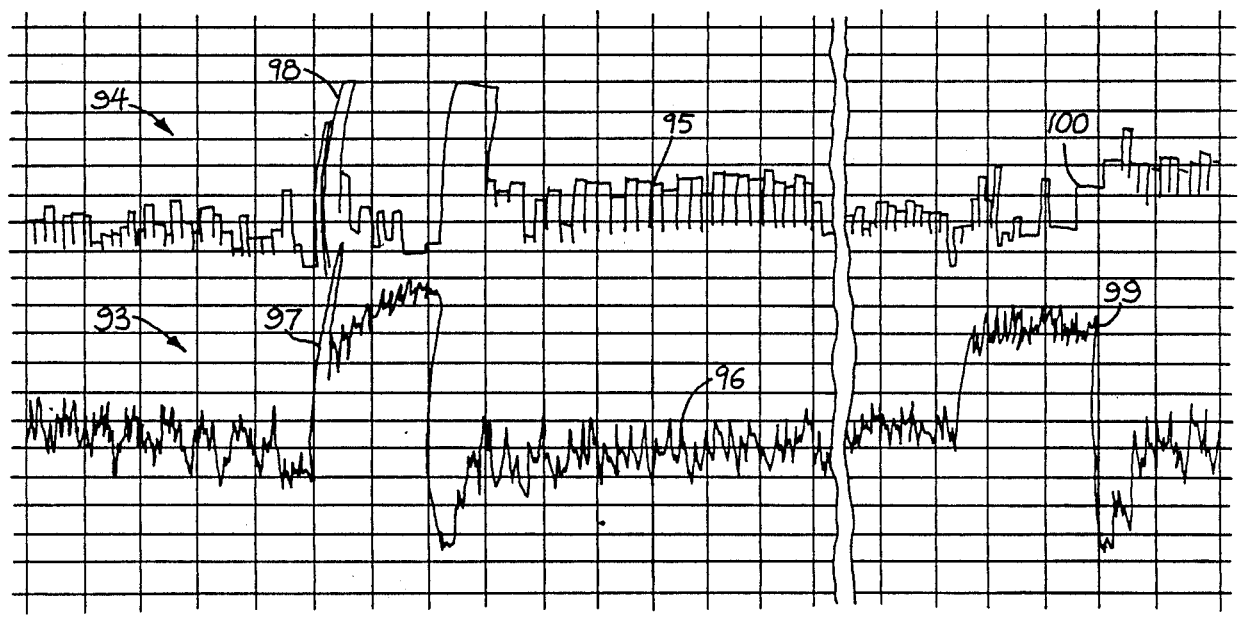
FIG. 6 is a diagram illustrating a record produced by the cardiac monitoring circuitry of FIG. 5.

The value being held by sample and hold circuit 86 is what is displayed on chart 10. FIG. 6 represents a diagram illustrating a record produced by the circuitry of FIG. 5. More specifically, FIG. 6 illustrates a blood pressure pulse waveform 93 and a dP/dt waveform 94. As shown, portion 95 of waveform 94 shows a smooth pattern associated with a subject being examined that corresponds to a smooth pattern of the subject's respiration and heart beat represented by the portion 96 of waveform 93. Portion 97 of waveform 93, however, represents a Valsalva meneuver by the subject, and corresponding portion 98 of waveform 94 illustrates the type of erratic pattern that would be produced by the circuitry of FIG. 5 in response to the Valsalva meneuver 97. Likewise, portion 99 of waveform 93 represents a different closed Glottal meneuver by the subject being examined, and portion 100 of waveform 94 represents the corresponding record which the circuitry of FIG. 5 would produce.

Figure 7:
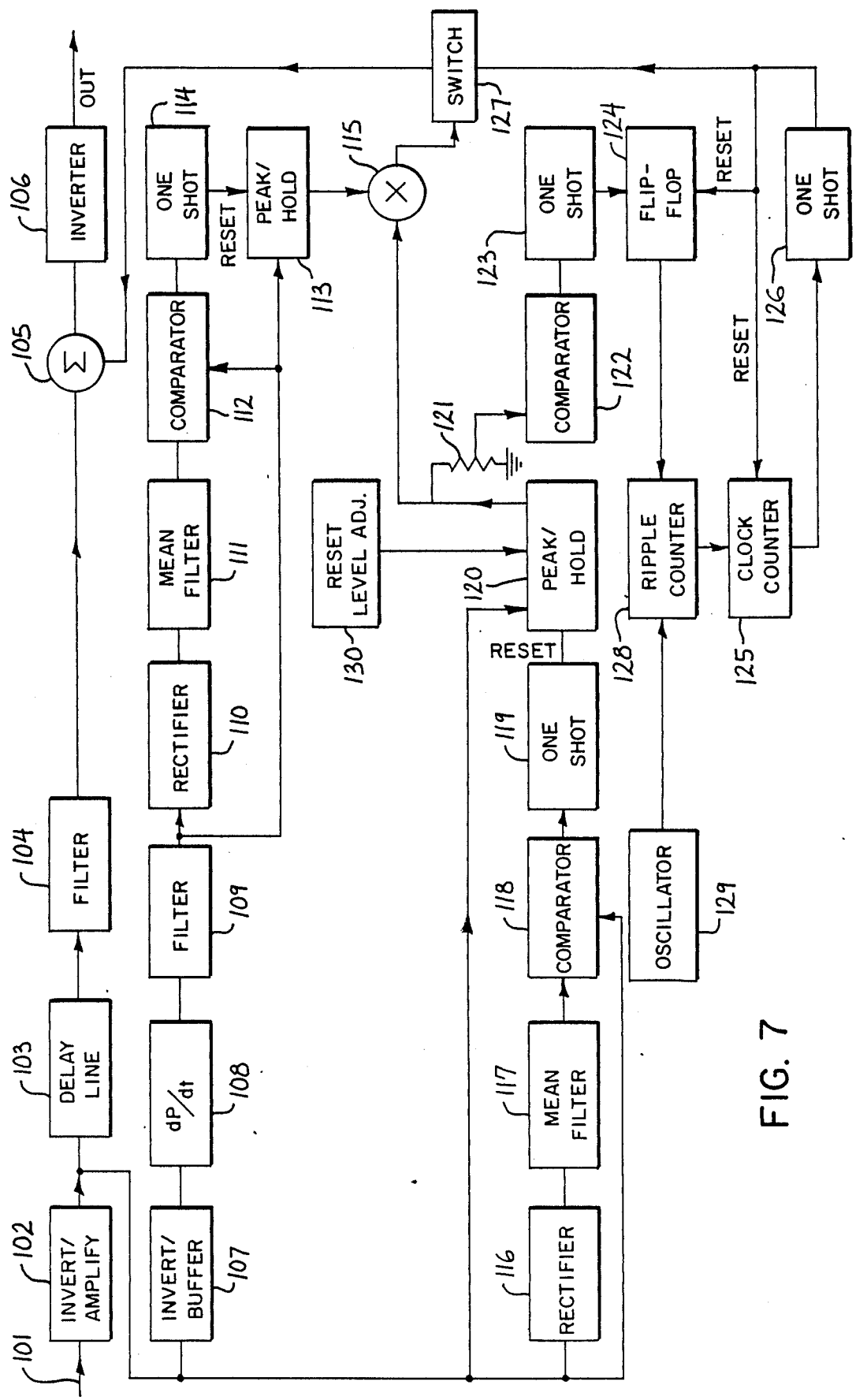
FIG. 7 is a block diagram of a third embodiment of the electronic circuitry for the cardiac monitoring apparatus of the present invention.

Referring now to FIG. 7, there is illustrated a block diagram of the electronic circuitry for a third embodiment of the cardiac monitoring apparatus of the present invention. Basically, the objective of this third embodiment is to take the dP/dt signal and add it to the top of the blood pressure pulse itself in order to simulate the pen overshoot of a mechanical cardio channel. In this embodiment, blood pressure pulse signal 101 from the cardio blood pressure cuff (not shown) is fed to an inverter/amplify circuit 102 in order to isolate and separate signal 101 from the normal amplifier circuitry of polygraph module 5 and also to shape signal 101 such that it is in an appropriate condition to be utilized by the remainder of the circuitry shown in FIG. 7. The output from circuit 102 is fed into a delay line circuit 103 which delays the pulse for an exact number of milliseconds. The output of delay line circuit 103 is then fed into a filter circuit 104 to remove any excessive noise generated by the delay line circuit 103. The output from filter circuit 104 is then fed into a summing amplifier 105 the output of which is inverted by inverter circuit 106 and fed into the polygraph channel for graphic display.

Blood pressure pulse signal 101 from circuit 102 is also fed into an invert/buffer circuit 107 which isolates signal 101 from the remaining portion of the circuitry shown in FIG. 7 as well as from the normal amplifier circuitry of polygraph module 5, and shapes the signal to a condition wherein it is appropriate for use by the remainder of the circuit. The output from circuit 107 is fed into a differentiator circuit 108 which detects the changing voltage level of signal 101 and is configured with gain to provide a derivative voltage out as the voltage of signal 101 changes. The output of differentiator circuit 108 is filtered by filter circuit 109 to remove noise, and then fed to a rectifier circuit 110 which causes the output voltage from differentiator circuit 108 to always be a positive signal. The output from rectifier circuit 110 is then fed to a mean filter circuit 111 to produce a mean dP/dt value. The mean dP/dt value from circuit 111 as well as the actual dP/dt value from differentiator circuit 108 are then both fed to a comparator circuit 112 which controls a peak and hold detector circuit 113, which functions as previously discussed herein with respect to the first two embodiments described. The output of comparator circuit 112 triggers a dual precision monostable multi-vibrator which is configured as a non-retriggerable one-shot 114 with its time constant adjustable via the RC time constant circuit thereof which is used to set and reset peak and hold detector circuit 113. The peak value held by circuit 113 is the peak of the actual dP/dt pulse signal, and as shown in FIG. 7 it's relative value is fed to an electronic multiplier 115.

Blood pressure pulse signal 101 is also fed to a rectifier circuit 116 which causes signal 101 to always be positive, and is then fed to a mean filter circuit 117 which produces a mean dP/dt level signal. The mean dP/dt level signal is then amplified by circuit 117 and is fed along with blood pressure pulse signal 101 to a comparator circuit 118 which triggers a dual precision monostable multi-vibrator which is configured as a non-retriggerable one-shot 119. One-shot 119 controls a second peak and hold detector circuit 120 which captures and holds the peak value of the blood pressure pulse signal 101. The output of peak and hold circuit 120, which is the peak value of blood pressure pulse signal 101, is then fed to multiplier 115 and also to a signal conditioning circuit 121 and then to a comparator circuit 122 which compares the peak value of the blood pressure pulse from peak and hold circuit 120 and the blood pressure pulse signal 101 itself. When the blood pressure pulse signal 101 falls below the peak value from circuit 120, comparator 122 is triggered indicating that the peak of the blood pressure pulse 101 has occurred. Comparator circuit 122 then triggers a dual precision monostable multi-vibrator which is configured as a non-retriggerable one-shot 123 which in turn triggers a flip flop circuit 124 which starts a clock counter 125. When clock counter 125 counts down to zero, it trips a one-shot 126 which closes a Motorola 4066 switch or similar device 127. As a result, summing amplifier 105 sums the value of the peak dP/dt level, scaled by multiplier 115 to the size of blood pressure pulse 101, to the delayed blood pressure pulse coming out of delay line circuit 103 and filter circuit 104. The tripping of one-shot 126 also resets flip flop circuit 124 and the count of clock counter 125. The timing signal into clock counter 125 is adjustable via a ripple counter 128 and oscillator 129. The adjustment of the timing signal allows setting of the trip point of switch 127 to anywhere in time so that the output of multiplier 115 can be summed by summer 105 to the delayed blood pressure pulse coming from delay line circuit 103 at any time during the blood pressure pulse. This allows putting the relative dP/dt value anywhere on the blood pressure pulse.

The input to multiplier 115 is the peak value of the blood pressure pulse coming from peak and hold circuit 113 and the peak value of the dP/dt pulse coming from peak and hold circuit 120. By multiplying these values together the size of the pulse that is added to the top of the blood pressure pulse is scaled to the size of the blood pressure pulse itself by a constant value. In this way, the relative size of the dP/dt value is always in proportion to the pulse that produced it even if its relative amplitude changes with changes in the strength of heart contraction. The setting of multiplier 115 allows the adjustment of the scale value so that the size of the dP/dt pulse on top of the blood pressure pulse can be adjusted. Once adjusted, the amplitude of the dP/dt pulse, on top of the blood pressure pulse, changes to show changes in the strength of contraction, relative to itself.

One-shot 126 is a dual precision monostable multivibrator which is configured as a non-retriggerable one-shot with its time constant adjustable via the RC time constant circuit thereof. The time constant of one-shot 126 that switches switch 127 sets the duration of the relative dP/dt signal amplitude as it is added to the top of the blood pressure pulse. By making the time constant of one-shot 126 longer, the width of the pulse that is added to the top of the blood pressure pulse is made greater.

The output from comparator circuit 122 which signals the arrival of the peak of the blood pressure pulse 101 is fed into one-shot 123 which is also a dual precision monostable multi-vibrator configured as a non-retriggerable one-shot that has its time constant adjustable via the RC time constant circuit thereof. Thus, the input of one-shot 123 has a time constant added to it to shape the pulse so that one-shot 123 is not double triggered by noise on the output from comparator 122. Thus, the output from one-shot 123 is a single sharp square wave which triggers flip flop circuit 124. This gives a single clock countdown per heart beat so that only one dP/dt signal is added to the top of the blood pressure pulse per heart beat. The above is also true with respect to peak and hold circuit 120 that is used to capture the peak dP/dt level. Circuit 120 is supplied with an adjustable reset level 130. This allows the reset level of peak and hold circuit 120 to be adjusted so that one-shot 123 is not double triggered by noise in the output from comparator circuit 122.

Figure 8A:
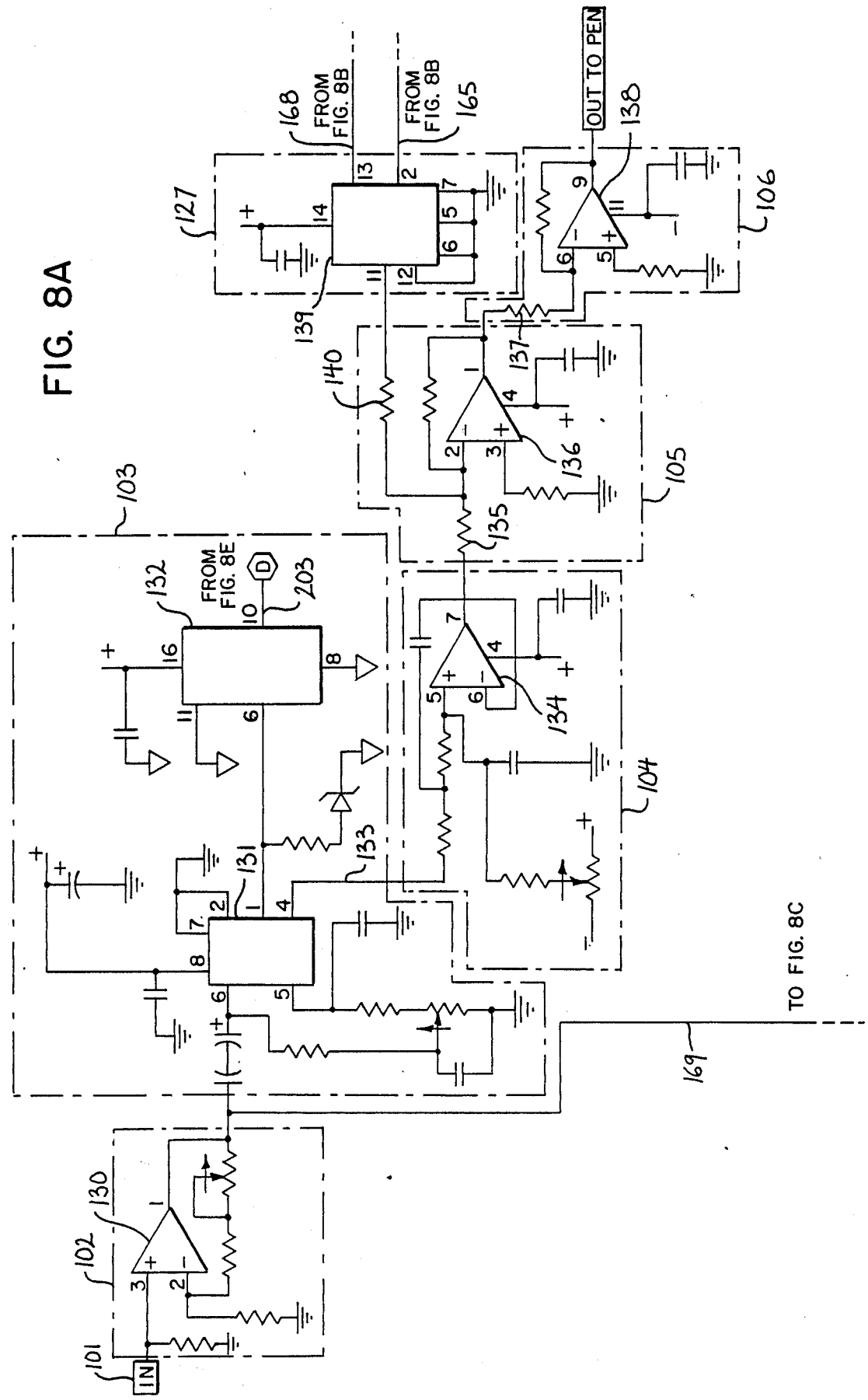
FIGS. 8A-8E are schematic diagrams of the electronic circuitry for the cardiac monitoring apparatus of FIG. 7.

Referring now to FIGS. 8A–8E there is schematically illustrated an electronic circuit for producing a waveform in accordance with the block diagram of FIG. 7. Referring specifically to FIG. 8A, blood pressure pulse signal 101 is received by invert/amplify circuit 102 which consists of a Linear Technology 1014 operational amplifier or a similar component 130 and is then fed to delay line circuit 103 which comprises an R5107 integrated circuit 131. The timing signal for integrated circuit 131 is provided by a 4040-2 binary counter 132 so that the pulse signal 101 entering integrated circuit 131 is delayed the desired time. The output from integrated circuit 131 which is the delayed blood pressure pulse is transmitted via line 133 to filter circuit 104 which comprises a 1014 operational amplifier or similar circuit 134. The output from amplifier 134 passes into summing circuit 105 which consists of a 1014 amplifier or similar circuit 136. The output from amplifier 136 passes to inverter circuit 106 which consists of a 1014 operational amplifier 138. The output from amplifier 138 then drives a pen motor (not shown) to produce the appropriate waveform. FIG. 8A also illustrates switch 127 which comprises a 4066 integrated circuit or similar circuit 139 the output of which is the peak value of the blood pressure pulse which is summed along with the delayed blood pressure pulse signal by summing circuit 105, as previously described herein with respect to FIG. 7.

Figure 8B:
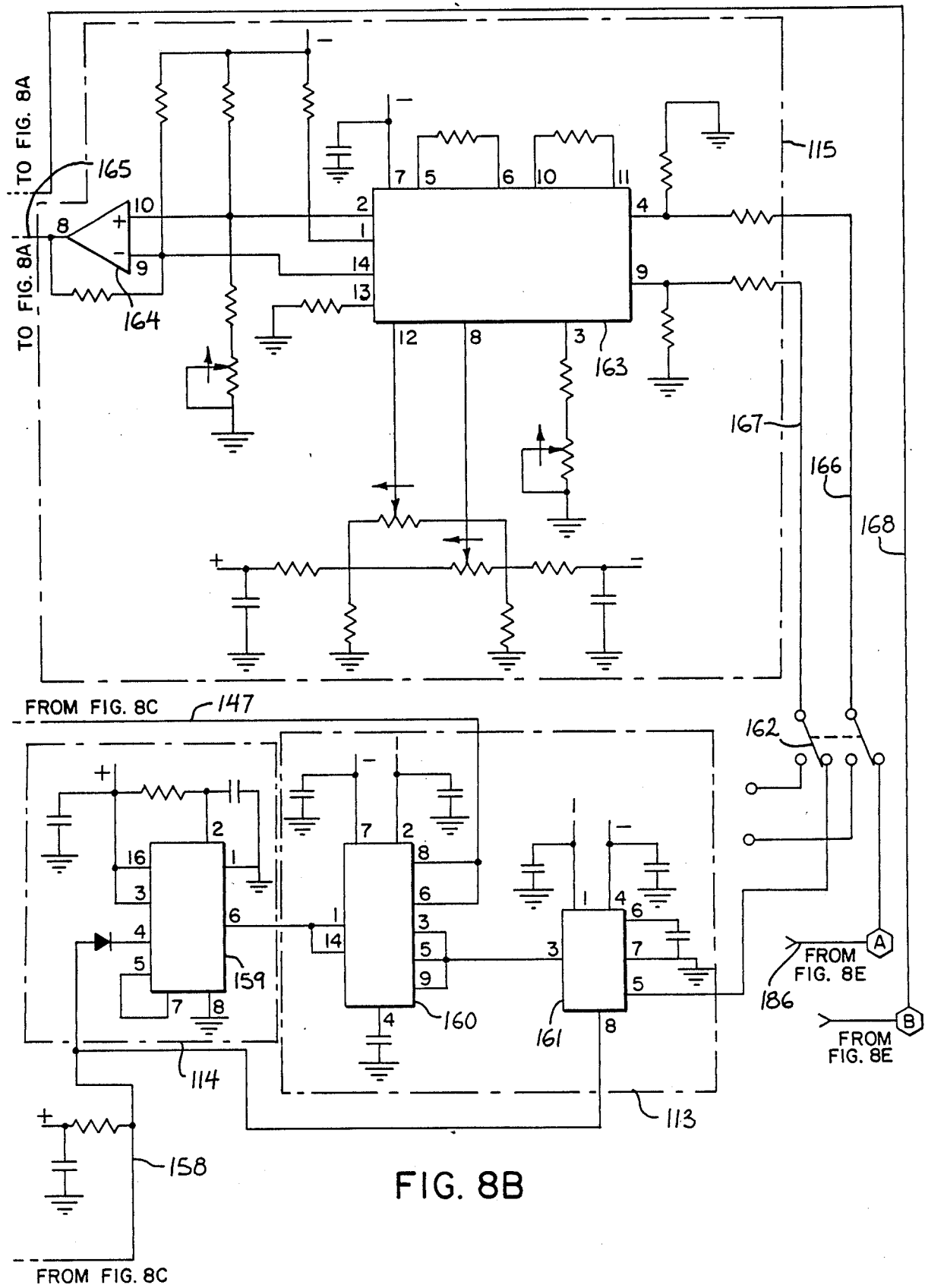
Figure 8C:
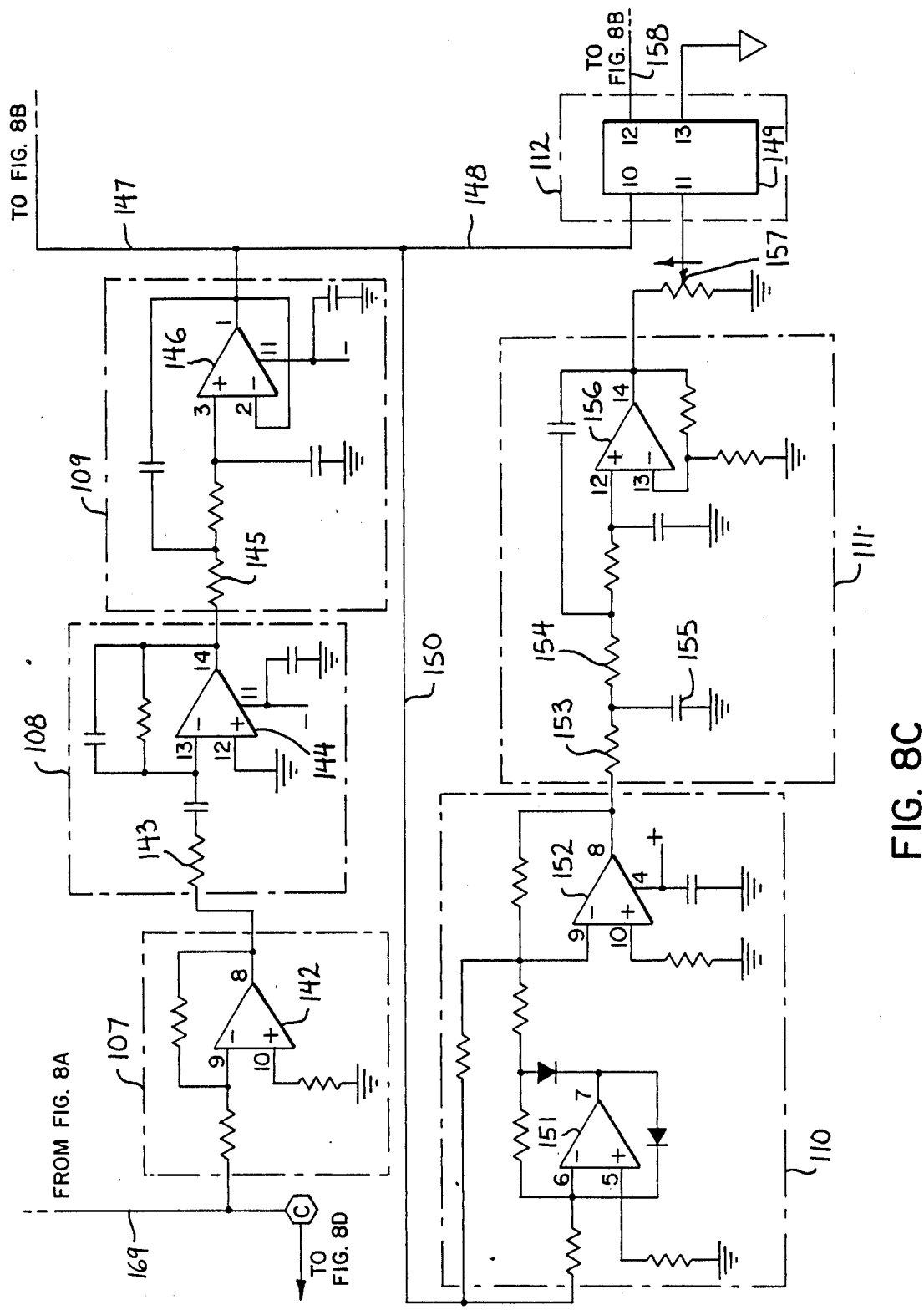

Blood pressure pulse signal 101 also is transmitted via line 169 (see FIG. 8A) to inverter/buffer circuit 107 (see FIG. 8C). Inverter/buffer circuit 107 includes a 1014 operational amplifier or similar circuit 142 the output of which passes to the input of differentiator circuit 108. Differentiatior circuit 108 includes a 1014 operational amplifier or similar circuit 144 the output of which passes to the input of filter circuit 109. Filter circuit 109 includes a 1014 operational amplifier or similar circuit 146 the output of which is transmitted via line 147 to peak and hold circuit 113 (see FIG. 8B), and also via line 148 to comparator circuit 112. Comparator circuit 112 is part of a PKD 01 integrated circuit 149 which is available from Precision Monolithics Company. The output from amplifier 146, which is the differential signal of the blood pressure pulse 101, is also transmitted via line 150 to the input of rectifier circuit 110. Rectifier circuit 110 includes two operational amplifiers of a 1014 operational amplifier or similar circuit 151 and 152. The output from amplifier 152 passes to the input of mean filter circuit 111. Circuit 111 includes a 1014 operational amplifier or similar circuit 156 the output of which is the mean dP/dt level which is transmitted to comparator circuit 112 and compared with the actual dP/dt level in line 148 by comparator 149. The trip point for comparator 149 may be adjusted by means of wiper 157.

The output of comparator 149 is transmitted via line 158 to the input of one-shot 114 (see FIG. 8B). One-shot 114 includes a 4538 integrated circuit or similar circuit 159. The output from integrated circuit 159 leads to the input of peak and hold circuit 113. Peak and hold circuit 113 includes a PKD01 integrated circuit or similar circuit 160 available from the Precision Monolithics Company as well as an LF398 integrated circuit or similar circuit 161 available from the National Semiconductor Company. Integrated circuit 160 detects the peak of the dP/dt signal while integrated circuit 161 performs the function of sampling and holding the peak dP/dt signal. The output from integrated circuit 161 is the peak value of the dP/dt pulse and is transmitted through miniswitch 162 to input pin 9 of a 1495 integrated circuit or similar circuit 163 contained within multiplier circuit 115. Multiplier circuit 115 also includes a 1014 operational amplifier or similar circuit 164 the output of which goes to switch 127 via line 165. It should further be noted that line 166 represents the peak value of the actual blood pressure signal 101 whereas line 167 represents the peak value of the dP/dt pulse from amplifier 161. Additionally, line 168 represents the signal from one-shot 126 that controls the closing of switch 127.

Figure 8D:
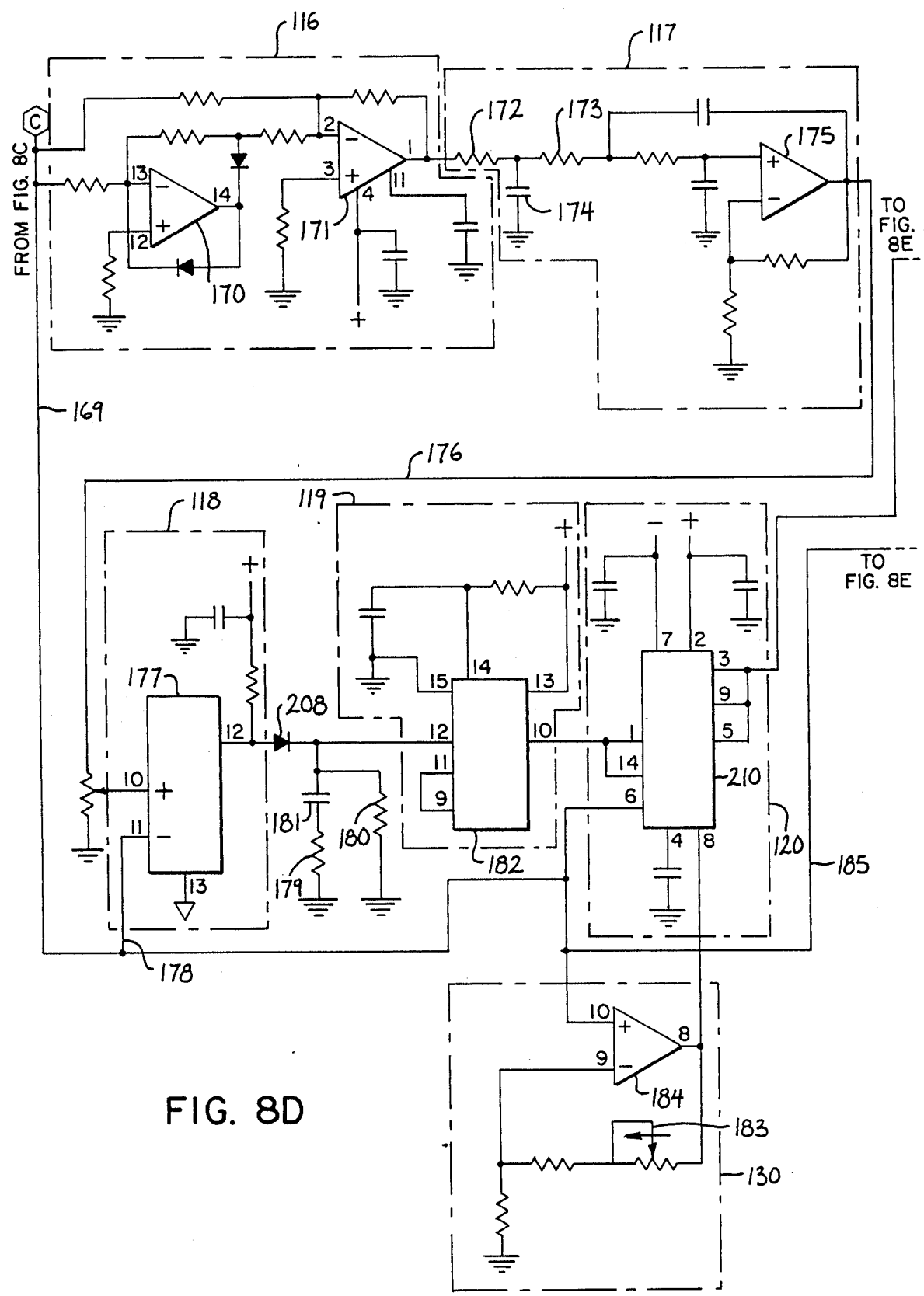

Referring now to FIG. 8D, blood pressure pulse signal 101 is also transmitted via line 169 to the input of rectifier circuit 116. Rectifier circuit 116 includes a pair of 1014 operational amplifiers or similar devices 170, 171, and the output therefrom passes to the mean filter circuit 117. Mean filter circuit 117 includes a 1014 operational amplifier or similar device 175 the output of which represents the mean blood pressure level and is transmitted via line 176 to the input of comparator circuit 118. Circuit 118 is included in a PKD01 integrated circuit 177 and compares the mean blood pressure level in line 176 with the actual blood pressure pulse in line 169 via line 178. The output from integrated circuit 177 is then filtered and shaped via resistors 179, 180, capacitor 181, and diode 208 and fed into one-shot 119. One-shot 119 comprises a 4538 integrated circuit or similar device 182 the output of which drives the peak and hold circuit 120. Peak and hold circuit 120 is included as part of the PDK01 integrated circuit 177, and is represented in FIG. 8D as integrated circuit 210. As shown in FIG. 8D, reset level adjustment circuit 130 includes an adjustable wiper 183 and a 1014 operational amplifier or similar device 184. Note that line 185 represents the actual blood pressure pulse signal 101 while line 186 represents the peak blood pressure value which is the output of integrated circuit 182.

Figure 8E:
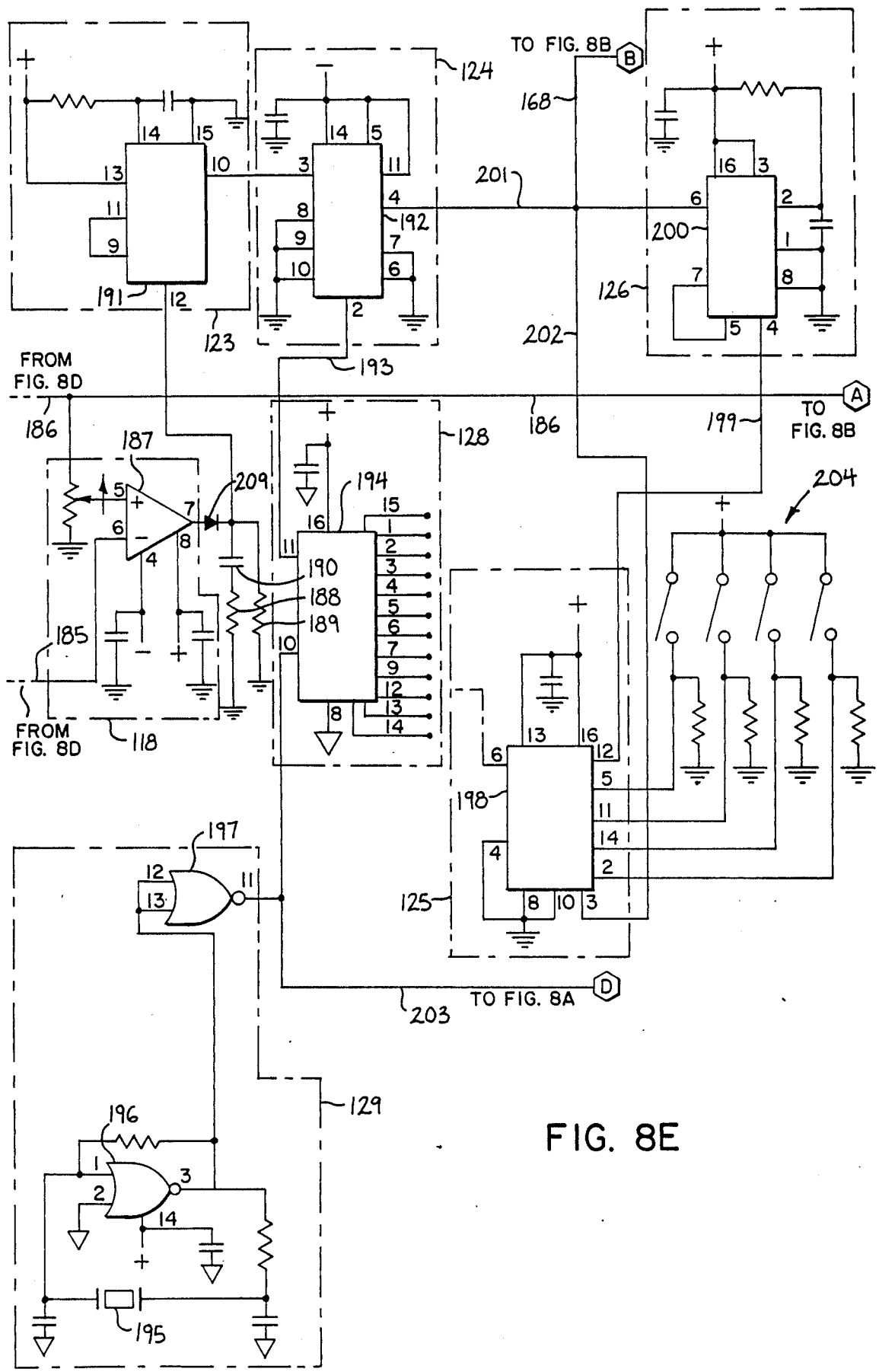

Referring now to FIG. 8E, the blood pressure signal in line 185 and the peak blood pressure signal in line 186 are both fed to opposite sides of a 1018 operational amplifier 187 of comparator circuit 118. The output from amplifier 187 is filtered by resistors 188, 189 capacitor 190, and diode 209 and then fed to the input of one-shot 123 which comprises a 4538 integrated circuit or similar circuit 191. The output from integrated circuit 191 triggers flip-flop circuit 124 which includes a 4013 integrated circuit or similar circuit 192. The output from integrated circuit 192 is transmitted to ripple counter 128 via line 193. Ripple counter 128 includes a 4040 integrated circuit or similar circuit 194 the timing of which is controlled by oscillator circuit 129 which includes a 100 KHz oscillator 195 and a 4001 Nor gate 196 the output of which also passes through another Nor gate 197 to ripple counter 128. The output of ripple counter 128 drives clock counter 125 which comprises a 4522 integrated circuit or similar circuit 198. The output from clock counter 125 fires one-shot 126 via line 199. One-shot 126 comprises a 4538 integrated circuit or similar circuit 200 the output of which resets flip flop 124 via line 201 and clock counter 125 via line 202. The output of one-shot 126 also is transmitted via line 168 to switch 127 (see FIGS. 8A and 8B). Note also that the peak blood pressure signal in line 186 is also transmitted through switch 162 and line 166 to integrated circuit 163 of multiplier 115. Note also that the timing signal from oscillator circuit 129 is transmitted via line 203 to binary counter 132 of the delay line circuit 103. Finally, frequency adjustment of integrated circuit 198 of clock counter 125 may be accomplished by means of a switch 204 (see FIG. 8E).

Figure 9:
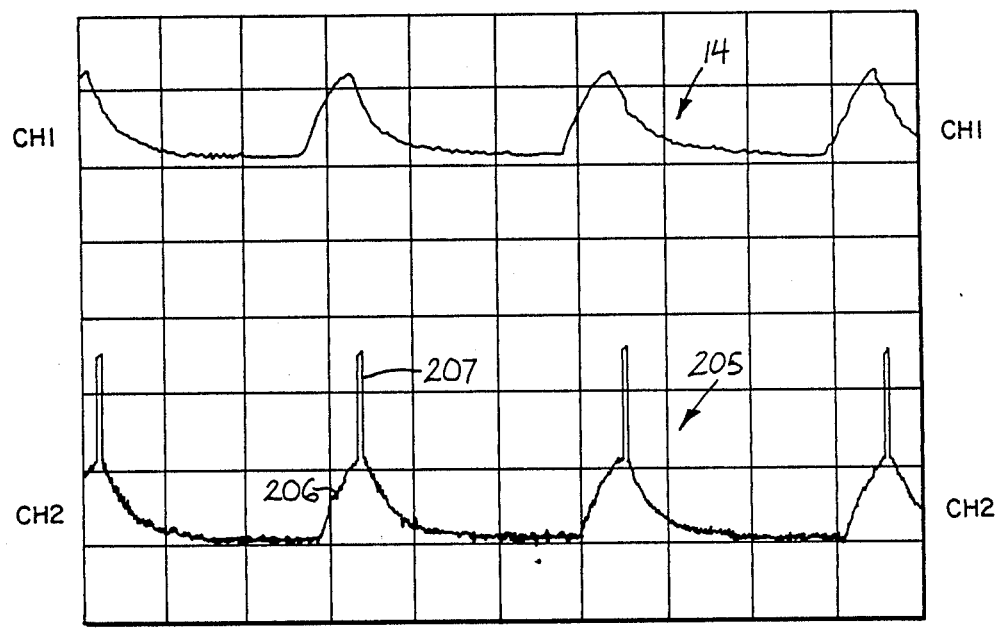
FIG. 9 is a diagram illustrating a record produced by the cardiac monitoring circuitry of FIGS. 8A-8E.

Referring now to FIG. 9, there is shown a diagram illustrating a record produced by the circuitry illustrated and described in FIGS. 7 and 8A-8E. As shown, channel 1 illustrates a typical waveform 14 used to represent the blood pressure pulse of a subject being examined. Channel 2 of the record shown in FIG. 9 illustrates a waveform 205 displayed as a result of the circuitry of FIGS. 8A-8E. Note that waveform 205 consists of a portion 206 corresponding to the shape of waveform 14 and a second portion 207 corresponding to a measurement of the rate of contraction of the heart which has been added to the top of portion 206 to simulate the pen overshoot found on a mechanical cardio channel.

A cardiac monitoring apparatus has been illustrated and described in order to detect and display the strength of contraction of the heart as an aid for indicating possible deception on the part of a subject being examined during a polygraph test. Three circuits to detect and display, by two different methods, the strength of contraction have been illustrated and described. Although specifically illustrated and described with respect to detecting the rate of increase of the blood pressure pulse, the present invention may be usable in connection with other measurements of information or attributes of the derivative pulse from respiration and/or skin resistance, depending upon the information desired.

Various modes of carrying out the invention are contemplated as being within the scope of the following claims particularly pointing out and distinctly claiming the subject matter which is regarded as the invention.

I claim:

1. A polygraph for detecting and recording physiological changes in an individual, comprising:

sensing means for sensing a physiological condition of an individual, said physiological condition representable by a periodic cyclic waveform having a leading upstroke portion and a trailing downstroke portion;

control means operatively connected to said sensing means for determining a rate of change over time of the upstroke portion of the waveform for said physiological condition; and display means operatively connected to said control means for displaying a signal indicative of said rate of change over time, wherein said sensing means produces a source voltage signal indicative of said condition, said display means includes a housing, a record chart on said housing, a pen engageable with said record chart, means for mounting said pen on said housing, and means for driving said pen on said chart, and said control means includes a control circuit operably connected to said pen driving means and responsive to the source voltage signal from said sensing means to provide a driving signal to said pen driving means, said control circuit includes differentiator means for detecting a change in the source voltage signal and for producing a differential signal having a waveform indicative of the source voltage signal change, said control circuit further includes measuring means for measuring a parameter which is characteristic of said differential signal waveform over a given time interval and for providing said driving signal, said time interval occurs at regularly spaced time periods, and said measuring means includes timing means for determining said time interval, wherein said time interval is periodic, and wherein said measuring means includes peak detector means for detecting a peak differential signal, and a sample and hold circuit means operable between a sample mode for receiving said peak differential signal and a hold mode for holding said peak differential signal.

2. The polygraph of claim 7 wherein said timing means is responsive to said measured parameter of said differential signal waveform to determine the duration of said time interval.

3. The polygraph of claim 8 wherein said timing means includes rectifier means for producing a mean differential signal, and comparator means for comparing said mean differential signal with said differential signal to produce a first timing signal to reset said peak detector means and a second timing signal to change said sample and hold circuit means between said sample mode and said hold mode.

4. The polygraph of claim 3 wherein said second timing signal trips said sample and hold circuit means into a hold mode prior to said first timing signal resetting said peak detector means.

5. The polygraph of claim 4 wherein said sensing means senses a blood pressure pulse signal said measuring means measures the rate of increase of the blood pressure pulse signal during a ventricular contraction, and said display means displays a waveform indicative of said rate of blood pressure pulse signal increase.

6. The polygraph of claim 5 wherein said control circuit further includes a summing circuit for adding said peak differential signal to said blood pressure pulse signal.

7. The polygraph of claim 6 wherein said summing circuit includes a delay circuit for receiving said blood pressure pulse signal and producing a delayed blood pressure pulse signal, summing means for summing said delayed blood pressure pulse signal and said peak differential signal, switch means operable between a closed position to turn on said summing means to permit summing of said delayed blood pressure pulse signal and peak differential signal and an open position to turn off said summing means, and a trigger circuit between said switch means and said blood pressure pulse signal for triggering said switch means at any desired time during the blood pressure pulse signal.

8. The polygraph of claim 7 wherein said summing means comprises a summing amplifier.

9. The polygraph of claim 7 wherein said trigger circuit triggers said switch means to its closed position at the peak of said blood pressure pulse signal.

10. The polygraph of claim 7 wherein said trigger circuit includes adjustable clock means for determining said any desired time.

* * * * *

UNITED STATES PATENT AND TRADEMARK OFFICE
CERTIFICATE OF CORRECTION

PATENT NO. : 4,940,059

DATED : July 10, 1990

INVENTOR(S) : Michael H. Voelz

It is certified that error appears in the above-identified patent and that said Letters Patent is hereby corrected as shown below:

Column 5, line 4:
    After "15a-15d" insert -- as well as --;

Column 12, line 60:
    After "through" insert -- a --;

Column 15, claim 2, line 1:
    Claim "7" should be -- claim 1 --;

Column 15, claim 3, line 5:
    Claim "8" should be -- claim 2 --.

Signed and Sealed this

Twenty-first Day of July, 1992

Attest:

DOUGLAS B. COMER

*Attesting Officer*       *Acting Commissioner of Patents and Trademarks*